United States Patent [19]

Lin et al.

[11] Patent Number: 5,047,494

[45] Date of Patent: Sep. 10, 1991

[54] CASTABLE POLYURETHANE ELASTOMERS CHAIN EXTENDED WITH 2,3-BIS(HYDROXYMETHYL)BICYCLO-[2,2,1-]HEPTANE

[75] Inventors: I. Sioun Lin, Mickleton, N.J.; Stanley J. Gromelski, Jr., Dover, Del.; Kou-Chang Liu, Wayne; Suzanne B. Nelsen, Mountain Lakes, both of N.J.

[73] Assignee: ISP Investments Inc., Wilmington, Del.

[21] Appl. No.: 394,908

[22] Filed: Aug. 17, 1989

[51] Int. Cl.$^5$ .............................................. C08G 18/32
[52] U.S. Cl. ........................................ 528/74; 528/64; 528/65
[58] Field of Search ............................... 528/64, 65, 74

[56] References Cited

U.S. PATENT DOCUMENTS

| | | |
|---|---|---|
| 2,941,967 | 6/1960 | Müller et al. ........................ 260/2.5 |
| 4,122,038 | 10/1978 | Sadrei et al. ...................... 252/431 C |
| 4,186,254 | 1/1980 | Cuscurida et al. .................... 521/115 |
| 4,350,778 | 9/1982 | Dominquez et al. ................ 521/118 |
| 4,510,269 | 4/1985 | Kopp .................................... 521/166 |
| 4,590,223 | 5/1986 | Arai ..................................... 521/118 |
| 4,927,976 | 5/1990 | Kou-Changhiu ..................... 568/665 |
| 4,948,866 | 8/1990 | Kou-Changhiu et al. ........... 528/272 |

*Primary Examiner*—John Kight, III
*Assistant Examiner*—Shelley A. Wright
*Attorney, Agent, or Firm*—Walter Katz; Marilyn J. Maue; Joshua J. Ward

[57] ABSTRACT

A castable polyurethane elastomer comprising the polymerization reaction product of a polyurethane prepolymer and 2,3-bis(hydroxymethyl) bicyclo [2,2,1] heptane as a chain extender. The elastomer has an advantageously low rebound property, which makes it particularly useful in shock absorber and anti-vibration mounting applications.

5 Claims, No Drawings

CASTABLE POLYURETHANE ELASTOMERS CHAIN EXTENDED WITH 2,3-BIS(HYDROXYMETHYL)BICYCLO[2,2,1]HEPTANE

BACKGROUND OF THE INVENTION

1. Field of the Invention

This invention relates to castable polyurethane elastomers which are chain extended with diols, and, more particularly, with polyurethane polymers which are chain extended with 2,3-bis(hydroxymethyl)bicyclo[2,2,1] heptane (BHMCH), to provide advantageous physical properties, particularly low rebound characteristics, for use in shock absorber and anti-vibration mounting applications.

2. Description of the Prior Art

Polyurethane compositions obtained by curing liquid isocyanate-terminated prepolymers are finding increased use in diverse applications requiring castable elastomers. Because of their inherent toughness, outstanding resistance to abrasion, oils, solvents, chemicals, oxidation, and the wide range of hardness and flexibility from soft, flexible elastomers to rigid plastic, they are frequently used in numerous applications such as: abrasion resistant coatings; coatings on metal or fabric for belting; flexible mechanical couplings, gears and drive wheels; mallet and hammer heads; rollers for printing and feed conveying; shock absorbent pads and bumpers; solid industrial truck tires and caster wheels; and the like.

The polyurethane elastomers are linear multiblock copolymers of the $(AB)_x$ type structure. They are typically formed as the reaction product of a diisocyanate with a hydroxyl terminated polyether or polyester polyol and a low molecular weight chain extender. The elastomeric properties of these materials arise from phase separation which leads to the formation of hard and soft segments. The soft segment consists of a long polyether or polyester chain with a molecular weight in the range of 1000–2000 while the hard segments are derived from the diisocyanate (MDI, i.e. 4,4'-diphenylmethane diisocyanate or TDI, i.e. tolylene diisocyanate) and low molecular weight chain extenders.

The most commonly used chain extenders for castable polyurethane elastomers are short chain diols, e.g. 1,4-butanediol ($B_1D$), cis-butenediol (cis-$B_2D$), trans-butenediol (trans-$B_2D$) and butynediol ($B_3D$). See Lin, I. et al. "$C_4$-Diol Chain Extenders in Castable and Rim Urethanes", J. Elastomers and Plastics 15, 57–80 (1983).

U.S. Pat. No. 3,492,330 describes the preparation of substituted norboranes for use in the manufacture of polymers. The substituted norborane compounds were made by free radical addition of a functionally substituted alkane to the unsaturated carbon atoms of a bridged-ring olefin. Among the bridged-ring olefins listed therein was the unsaturated diol produced by a Diels-Alder reaction between cyclopentadiene and butenediol. Subsequent reaction of the unsaturated diol with a functionally substituted alkane at the position of unsaturation produced the desired substituted norborane. However, there was no description of a corresponding saturated diol (BHMCH) or of its use as a chain extending agent in the manufacture of new and useful castable polyurethane elastomers.

Birch, S. et al. in the J. Org. Chem. 21, 970–974 (1956) described the preparation of BHMCH by a three-step process. The disclosed process comprised a Diels-Alder condensation of cyclopentadiene and maleic anhydride to form an unsaturated anhydride, reduction of the anhydride with lithium aluminum hydride to produce the unsaturated diol, and hydrogenation of the ethylenic bond to produce the saturated diol, i.e. BHMCH. However, BHMCH was used merely to provide the corresponding sulfur analogs.

Accordingly, there is a need for novel castable polyurethane elastomers having advantageous physical properties which are products of polyurethane prepolymers and derivatives of short chain diols, in particular, derivatives of $C_4$-diols, for use as chain extenders of polyurethane prepolymers.

An object of this invention, therefore, is to provide such advantageous castable polyurethane elastomers.

A specific object herein is to provide castable polyurethane elastomers having low rebound properties for use in shock absorbant pads and anti-vibration mounting applications.

SUMMARY OF THE INVENTION

What is provided herein are castable polyurethane elastomers comprising the polymerization reaction product of a polyurethane prepolymer and 2,3-bis (hydroxymethyl) bicyclo [2,2,1] heptane as a chain extender.

The castable polyurethane elastomer products of the invention have advantageous physical properties, particularly a low rebound characteristic.

DETAILED DESCRIPTION OF THE INVENTION

1. Preparation of Chain Extender (BHMCH)

The chain extender of the invention is prepared by a one-pot, two-step synthesis in a non-toxic solvent according to the following scheme:

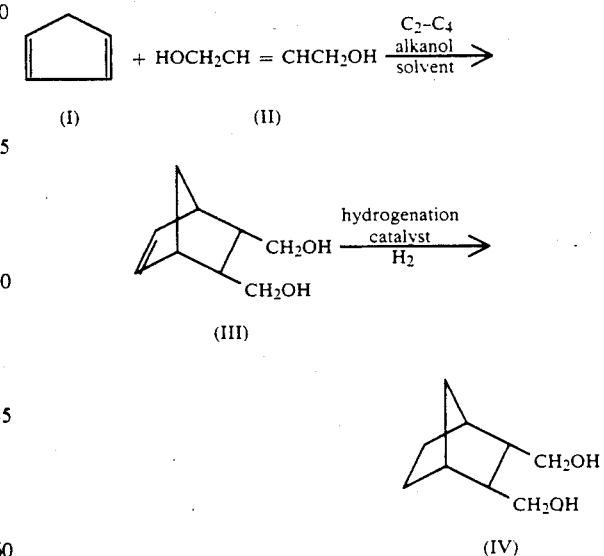

Accordingly, cyclopentadiene (I) and 2-butene-1,4-diol (II), in a molar ratio of about 0.5:1 to 2:1, respectively, are heated at a temperature of about 140° to 200° C., for about 5 to 20 hours, in a $C_2$–$C_4$ straight or branched chain alcohol solvent, e.g. ethanol, at a solvent level of about 20 to 200% by weight of the reaction mixture, to produce the unsaturated diol intermediate (III). In the same pot and alcohol solvent, (III) is hydrogenated at a temperature of about 50° to 200° C., for about 1 to 20 hours, with a hydrogenation catalyst, to produce the saturated diol (IV). Generally the catalyst comprises about 0.05 to 5% by weight of (III). Suitable hydrogenation catalysts include palladium, platinum, rhodium and the like, which may be supported or unsupported. Suitable supports include charcoal, calcium carbonate and the like.

The process of the invention provides the desired 2,3-bis (hydroxymethyl) bicyclo [2,2,1] heptane (BHMCH) chain extender in yields of 75% or more.

The chain extender of the invention is particularly adapted to cross-link with an isocyanate prepolymer and to effect polymer cure, thus provididng a cured product of significantly improved physical properties. A melt of the chain extender is combined with a polyurethane prepolymer at a temperature of between about 70° and about 120° C. under atmospheric pressure by stirring the chain extending agent and prepolymer for a period of from about 30 seconds to about 2 minutes.

The polyurethane prepolymers of this invention include both polyalkylene ether glycol- and polyester glycol-based polyurethanes and have a free NCO content of from about 2.5 to about 12 weight %. A typical example of the former is Adiprene ® M-400 (duPont). The free isocyanate content of this prepolymer is about 7.5%. Another example is Adiprene ® M-467 which has a free isocyanate content of about 9.6%.

Polyurethane prepolymers can be based on other polyalkylene ether glycols, e.g. polypropylene ether glycols and mixed polyalkylene ether glycols obtained by condensation of ethylene oxide, 1,2-propylene oxide and 1,2-butylene oxide with glycols having more than two carbon atoms.

Generally, these polyether glycols can be prepared by the polymerization of cyclic ethers, such as tetrahydrofuran or epoxides or by the addition of epoxides to glycols, dihydroxyethers, dihydroxythioethers, dihydric phenols and the like by known methods. Polyalkylene ether glycols suitable for the preparation of polyurethane prepolymers should have a molecular weight of at least 500, up to about 10,000; although molecular weights of about 750 to 3000 are preferred. Optionally, glycols having molecular weights of less than abut 350 can be added to the high molecular weight glycols. These low molecular weight glycols can be used in proportions of about 0.5-3.0 moles per mole of polyether glycol; however, exact proportions are determined by the desired physical properties of the final products. Representative glycols of this type include ethylene glycol, 1,2-propylene glycol, 1,2-butylene glycol, 1,3-butanediol, 1,4-butanediol, 1,5-pentanediol, 1,10-decanediol, 3-cyclohexene-1,1-dimethanol, diethylene glycol, dipropylene glycol, and the like. Mixtures of two or more of these low molecualr weight glycols may be used.

Polyurethane prepolymers which can be employed in the process of this invention can also be based on polyester glycols, such as poly(ethylene adipate), poly(ethylene/propylene adipate), poly(ethylene glutarate) and poly(ethylene pimelate). Multrathane F-242 supplied by Mobay is an example of a commercially available polyester-based methylene diparaphenylene diisocyanate which is beneficially employed in the present invention.

Polyester glycols suitable for the preparation of polyurethane prepolymers can be made by several alternate routes, such as, condensation of a dicarboxylic acid with an excess of a diol, transesterification of a dicarboxylic acid ester of a lower alcohol with a diol, or reaction of dicarboxylic acid dichloride with a diol, optionally in the presence of a proton acceptor. Aliphatic dicarboxylic acids and alkanediols are preferred because of the desirable physical properties of the final products. However, aromatic dicarboxylic acids, such as terephthalic acid, and dihydric phenols, such as hydroquinone or resorcinol, also can be used in the preparation of polyester glycols suitable for making polyurethane prepolymers. Generally, the above described polyester glycols should have a molecular weight of 500-10,000, a molecular weight of 750-3000, being preferred.

Polyurethane prepolymers are made by reaction of a polyalkylene ether glycol or a polyester glycol with an excess of an organic diisocyanate. Because of their greater reactivity, aromatic diisocyanates are preferred but aliphatic or araliphatic diisocyanates also can be used. Representative isocyanates include toluene-2,4-diisocyanate, toluene-2,6-diisocyanate, benzene-1,3-diisocyanate, naphthalene-1,5-diisocyanate, methylene bis(4-phenyl isocyanate), 4,4′-biphenylene diisocyanate, hexamethylene diisocyanate, 1,4-cyclohexane diisocyanate, and methylene-bis(4-cyclohexane isocyanate). Of course, mixtures of two or more diisocyanates may be employed.

Using the present chain extender, lower rebound properties are obtained with polyurethane prepolymers than achieved with conventional diol chain extenders.

Generally, useful polyurethane elastomers can be obtained by employing the chain extender of this invention in amounts such as 95% to 105% of stoichiometry. Most desirably, stoichiometry is maintained at about 95% based on prepolymer content. Prepolymers are preheated at 70° to 120° C. and mixed with the present chain extender at between about 50° C. and about 100° C. Minor modifications in mixing temperatures may be made to suit individual needs. The prepolymer, curative and prepolymer-curative mixture are each vacuum degassed prior to pouring the mixture into a mold preheated to between about 70° C. and about 120° C. Degassing before and after mixing is especially important to achieve bubble-free castings. The mold is closed when gelation has started. Working life can be expected to decrease rapidly when catalyst is added to the formulation.

Having generally described the invention, reference is now had to the examples which illustrate specific and preferred embodiments of the invention; however, these embodiments are not to be construed as limiting to the scope which is properly defined in the foregoing description and disclosure and in the appended claims. In the examples which follow, all amounts and proportions are by weight unless otherwise indicated.

EXAMPLE 1

Preparation of 2,3-Bis (Hydroxymethyl) Bicyclo [2,2,1] Heptane

Cyclopentadiene (150 g., 2.28 moles), 2-butene-1,4-diol (150 g., 1.7 moles) and ethanol (300 g.) were charged into a 1-liter stainless steel autoclave. The autoclave was purged three times with nitrogen at 100 psig and then heated to 175° C. for 10 hours. After being cooled to room temperature, 3 g. of 5% Pd on charcoal was added to the mixture. The mixture was purged two times with nitrogen, heated to 170° C. and hydrogenated at 100 psig. The hydrogenation was completed in 7 hours.

The crude product was filtered to remove the catalyst and rotoevaporated to remove ethanol. The semisolid material obtained was distilled at 0.3-0.5 mm of Hg. The desired product comprised a forecut of 32.7 g. of material and a center cut of 150.1 g. of a pale yellow solid (m.p. 52°-56° C). The solid was recrystallized from 100 ml toluene-50 ml hexane to give 124 g. of white solid; m.p. 57°-60° C., which was identified by NMR as the title compound.

EXAMPLE 2

Preparation of Castable Polyurethane Elastomer 100 parts by weight of a polyester-based MDI prepolymer* was degassed at 93° C. for 40 minutes and 11.8 parts by weight (0.076 mole) of 2,3,bis-(hydroxymethyl) bicyclo[2,2,1] heptane (BHMCH) (Eq. wt. 78) was degassed at 70° C. prior to mixing with prepolymer. The prepolymer and chain extender were mixed and poured into a mold preheated to 110° C. The curing time in the mold was 40 minutes. The resulting plaque was post-cured for 16 hours at 100° C. and then conditioned for one week at 50% relative humidity at room temperature.

* Mobay's Multrathane F-242 Polyester 4,4'-diphenylmethane diisocyanate (MDI) prepolymer (6.7±0.1% NCO).

EXAMPLE 3

Properties of Polyurethane Elastomer of Example 2

| Physical Properties | |
| --- | --- |
| Rebound Characteristics | |
| Bashore Rebound, % | 7 |
| Other Properties | |
| Hardness, Shore A | 62 |
| Shore D | 20 |
| 100% Modulus, psi | 283 |
| 300% Modulus, psi | 497 |
| Tensile strength, psi | 3580 |
| Elongation, % | 519 |
| Tear strength, psi | 194 |
| Compression Set, 22 hrs./70° C., Method B | 15 |

COMPARATIVE EXAMPLES 4-6*

| Ex. | Chain Extender | Amt., Moles | Bashore Rebound, % |
| --- | --- | --- | --- |
| 3 | BHMCH | 0.076 | 7 |
| 4 | 1,4-Butanediol | 0.074 | 47 |
| 5 | 2-Butene-1,4-diol | 0.077 | 41 |
| 6 | 2-Butyne-1,4-diol | 0.076 | 20 |

*Formulated with 100 g. of Multrathane F-242 and processed as in Example 1.

* Formulated with 100 g. of Multrathane F-242 and processed as in Example 1.

The test results above demonstrate that the castable polyurethane elastomer of the invention formulated with the chain extender BHMCH of the invention exhibits a rebound characteristic which is about 3-7 times less than the corresponding elastomers prepared using $B_1D$, $B_2D$ or $B_3D$ chain extenders. The BHMCH chain extended polyurethane elastomers of the invention thus provide improved shock absorbent pads and anti-vibration mountings in commercial application than simpler diols.

Although the invention has been described with reference to certain embodiments thereof, it will be understood that changes and modifications may be made which are within the skill of the art.

What is claimed is:

1. A castable polyurethane elastomer comprising the polymerization reaction product of a polyurethane prepolymer and 2,3-bis (hydroxymethyl) bicyclo [2,2,1] heptane.

2. The elastomer of claim 1 wherein said polyurethane prepolymer is a polyester methylene diparaphenylene diisocyanate which has a Bayshore Rebound % of about 7.

3. A process for preparing a castable polyurethane elastomer which comprises admixing a polyurethane prepolymer and 2,3-bis (hydroxymethyl) bicyclo [2,2,1] heptane at a temperature between about 70° C. and 120° C.

4. A process according to claim 3 wherein the reactants are admixed for a period not longer than about 2 minutes.

5. A shock absorber or an anti-vibration mounting comprising the castable polyurethane elastomer of claim 1.

* * * * *